US008283336B2

(12) United States Patent
Groenendijk et al.

(10) Patent No.: US 8,283,336 B2
(45) Date of Patent: Oct. 9, 2012

(54) UNIT DOSAGE FOR BRAIN HEALTH

(75) Inventors: Martine Groenendijk, Barendrecht (NL); Robert Johan Joseph Hageman, Wageningen (NL); Patrick Joseph Gerardus Hendrikus Kamphuis, Utrecht (NL); Erwin Peke Meijer, Wageningen (NL)

(73) Assignee: N. V. Nutricia, Zoetermeer (NL)

( * ) Notice: Subject to any disclaimer, the term of this patent is extended or adjusted under 35 U.S.C. 154(b) by 346 days.

(21) Appl. No.: 12/740,435

(22) PCT Filed: Oct. 27, 2008

(86) PCT No.: PCT/NL2008/050672

§ 371 (c)(1), (2), (4) Date: Apr. 29, 2010

(87) PCT Pub. No.: WO2009/058005

PCT Pub. Date: May 7, 2009

(65) Prior Publication Data

US 2010/0261669 A1 Oct. 14, 2010

(30) Foreign Application Priority Data

Nov. 2, 2007 (WO) ................ PCT/NL2007/050529

(51) Int. Cl.
*A01N 43/04* (2006.01)
*A61K 31/70* (2006.01)

(52) U.S. Cl. ................. 514/49; 514/43; 514/50; 514/51

(58) Field of Classification Search ........................ None
See application file for complete search history.

(56) References Cited

U.S. PATENT DOCUMENTS 5,066,500 A 11/1991 Gil et al.
5,780,081 A 7/1998 Jacobson et al.
5,792,501 A 8/1998 Lepine
6,245,379 B1 6/2001 Lepine
6,420,342 B1 7/2002 Hageman et al.
2001/0007878 A1 7/2001 Lowry et al.
2003/0054083 A1 3/2003 Gohman et al.
2003/0060445 A1 3/2003 Wilson
2007/0098849 A1 5/2007 Barrett-Reis et al.
2008/0125346 A1 5/2008 Beerman

FOREIGN PATENT DOCUMENTS

AU 200022638 A1 6/2000
CA 2 428 473 A1 5/2002
EP 0 483 070 A3 4/1992
EP 0 756 828 B1 2/1997
EP 1 666 092 A2 6/2006
EP 1 800 675 A1 6/2007
EP 1 803 358 A1 7/2007
WO WO 2006/031683 A2 3/2006
WO WO 2006/127620 A2 11/2006
WO WO 2007/008586 A2 1/2007

OTHER PUBLICATIONS

O. Hansson et al., "Association Between CSF Biomarkers and Incipient Alzheimer's Disease in Patients with Mild Congnitive Impairment: A Follow-up Study," Lancet Neurology, 2006, vol. 5, pp. 228-234.
D. Pratico et al., "Increase of Brain Oxidative Stress in Mild Cognitive Impairment," Arch Neurol, vol. 59, Jun. 2002, pp. 972-976.
Search Report mailed Apr. 11, 2006 in International Application No. PCT/NL2005/000609.
Search Report mailed Jan. 24, 2005 in European Application No. 04019856.6.
Search Report mailed Jul. 31, 2008 in International Application No. PCT/NL2007/050529.
US Office Action mailed Jun. 29, 2010 in U.S. Appl. No. 11/573,939.
US Office Action mailed Oct. 8, 2009 in U.S. Appl. No. 11/573,939.
US Office Action mailed Apr. 21, 2009 in U.S. Appl. No. 11/573,939.
International Search Report mailed Jun. 8, 2009, in PCT/NL2008/050672, 4 pages.
Grundman, Michael, "Vitamin E and Alzheimer disease: the basis for additional clinical trials," Am. J. Clin. Nutr., Feb. 2000, 71(2):630S-636S.
Ricciarelli et al., "Vitamin E and neurodegenerative diseases," Molecular Aspects of Medicine, Oct. 1, 2007, 28(5-6):591-606.

*Primary Examiner* — Patrick Lewis
(74) *Attorney, Agent, or Firm* — Gilberto M. Villacorta; Sunit Talapatra; Foley & Lardner LLP

(57) ABSTRACT

The invention pertains to a composition comprising (i) uridine in nucleobase, nucleoside and/or nucleotide form; (ii) docosahexaenoic acid (DHA) and/or eicosapentaenoic acid (EPA); and (iii) a tocopherol and/or an equivalent thereof, wherein said composition has: a) a weight of 200-3000 mg per unit dose; b) an energy content of less than 50 kcal per unit dose; and/or c) a volume between 0.1 and 10 ml per unit dose. The invention also pertains to the use of such composition in reducing abeta plaque burden and neurodegeneration, in the treatment of diseases related with imparted nerve functioning, in particular dementia, Alzheimer's disease and memory disorders.

16 Claims, 3 Drawing Sheets

UNIT DOSAGE FOR BRAIN HEALTH

CROSS-REFERENCE TO RELATED APPLICATIONS

This is a National Stage application of PCT/NL2008/050672, filed Oct. 27, 2008, which claims the benefit and priority of PCT/NL2007/050529, filed Nov. 2, 2007. The foregoing applications are incorporated by reference herein in their entirety.

FIELD OF THE INVENTION

The invention pertains to compositions and methods for treating or preventing memory dysfunction, cognitive dysfunction, Alzheimer's and dementia, and pre-dementia-related conditions and/or symptoms or characteristics of such conditions. The invention particularly relates to low-volume administration forms for use therein.

BACKGROUND OF THE INVENTION

Memory loss, dementia and reduced brain function are major problems, particularly in elderly. Significant effort is put in the treatment and/or prevention of these disorders related with impaired nerve functioning.

Persons older than 50 years of age are particularly prone to developing such disorders, by a combination of aging and non-optimal nourishment. These syndromes, generally known as dementia or Alzheimer's disease (AD), are characterized by neurodegeneration and the deposition of plaques in the brain. These plaques consist of a number of components of which beta-amyloid (abeta) is seen as a key element. Abeta is produced from its precursor protein which resides in the membrane, and is believed to promote pro-inflammatory responses and to activate neurotoxic pathways causing neuronal dysfunction characterized by a loss of spines and neurites leading to neuronal death.

WO 2007/008586 A2 (Martek Biosciences Corp.) and EP 1 800 675 A1 (Nutricia N.V.) describe compositions for the treatment and/or prevention of dementia, wherein the composition comprises a lipid fraction comprising polyunsaturated fatty acids (PU-FAs) such as docosahexaenoic acid (DHA) or docosapentaenoic acid (DPA).

It has also been shown in WO 2006/031683 A2 (MIT) to administer uridine or a source thereof in order to improve a neurological function in a subject. Uridine, in particular in the form of uridine monophosphate (UMP), is a nutrient that is known to increase the production of phospholipids, thus changing the membrane composition. However, at present no effects of UMP on abeta plaque burden have been reported.

Compositions comprising a uridine nucleoside/nucleotide and a fatty acid, in particular EPA and/or DHA have been disclosed in EP 1 666 092 A2 (Trommsdorff GmbH) for treating a variety of diseases among which neurodegenerative disease such as Alzheimer's Disease, and in WO 2006/127620 A2 (MIT) for the treatment of a memory disorder.

SUMMARY OF THE INVENTION

Based on foregoing, one may expect intervention with a mixture of nutrients such as DHA and UMP to result in an effective strategy to decrease neurodegeneration. However, the present inventors have recognized that inclusion of active ingredients UMP and DHA in nutritional and pharmaceutical compositions as taught in the art may result in an insufficient intake of these active ingredients. The insufficient intake is caused by a combination of a high volume of the nutritional product in combination with the limited appetite of the (elderly) patients, with the result that the recommended dosage of active ingredients (often included in 100-500 ml nutritional product) is not ingested. Hence, inclusion of the active ingredients in a nutritional composition may result in a suboptimal effect in patients with reduced appetite or disturbed eating behaviour, or rejection of food.

It would be a straightforward alternative to reduce the dosage volume by incorporating the active ingredients in a low-volume dosage form, e.g. a pill, tablet or capsule. However, due to the low volume, some ingredients in the compositions taught in the art must be left out. The present inventors found however that eliminating (nutritional) ingredients from the nutritional composition (such as e.g. described in example 1 of EP 1 800 675 A1), and only administering the UMP and DHA, may result in a low-volume dosage form, but unfortunately at the cost of the neurodegenerative effect (beta amyloid). In fact, as demonstrated in the accompanying examples, it may even have an adverse effect on neurodegeneration. Hence simply incorporation and administration of UMP and DHA in a low-volume dosage form is not optimal.

In the art, a need thus exists for producing low-volume dosage forms for reducing abeta plaque burden and decreasing neurodegeneration, wherein the effects of the active ingredients are at least similar to those found for full nutraceutical and pharmaceutical formulations.

It is an objective of the present invention to provide a low-volume dosage form for use in reducing abeta plaque burden and neurodegeneration, in the treatment of diseases related with imparted nerve functioning, in particular dementia or AD or memory disorders.

Therein, the present inventors surprisingly found that inclusion of a tocopherol and/or an equivalent thereof (i.e. a compound having vitamin E activity) overcome the aforementioned disadvantages related with DHA and UMP in low-dosage formulation. This new finding thus enables the manufacture of low dosage composition that can be effectively used for the treatment and/or prevention of memory decline and/or cognitive dysfunction and/or support of healthy brain function, as discussed below in more detail.

The administration of vitamin E for the treatment of Alzheimer's Disease has been described by Grundman in *The American Journal of Clinical Nutrition,* 71 (2), 630S-636S (2000) for reduction of oxidative stress, and by Ricciarelli et al. in Molecular Aspects of Medicine, 28, 591-606 (2007) for the treatment of neurodegenerative diseases. However, none of these publications disclose nor suggest the combined use and the specific compositions according to the present invention. Experiment 2 in the accompanying examples does not show an effect of alpha-tocopherol alone.

DETAILED DESCRIPTION OF THE INVENTION

Figure 1A:
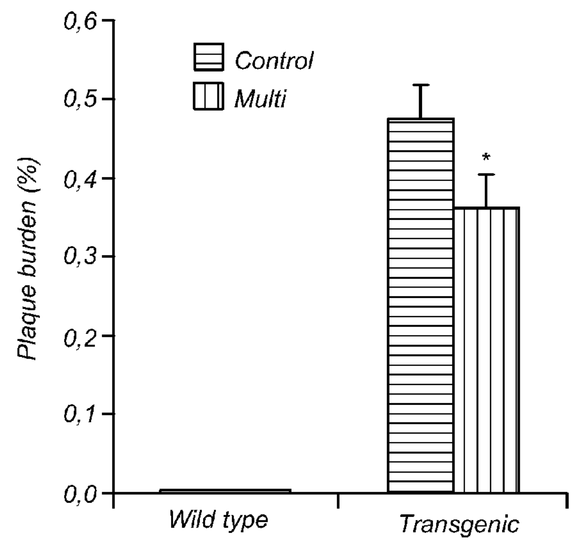
FIG. 1A shows the percent plaque burden in the hippocampus of wild-type and APP/PS1 transgenic mice fed a control diet or one comprising UMP, DHA, and alpha-tocipherol ("multi").

The invention thus pertains to a composition comprising (i) uridine in nucleobase, nucleoside and/or nucleotide form; (ii) docosahexaenoic acid (DHA) and/or eicosapentaenoic acid (EPA); and (iii) a tocopherol and/or an equivalent thereof, wherein said composition has:

a) a weight of 200-3000 mg per unit dose;

b) an energy content of less than 50 kcal per unit dose; and/or c) a volume between 0.1 and 10 ml per unit dose.

Administration Form

For reasons stated above, the low-volume composition distinguishes from nutritional and dietary compositions (nutraceuticals) and nutritional supplements. The composition may involve the presence of one or more conventional carriers and/or diluents.

The composition is in the form of a unit dose. Unit doses are defined as physically identifiable separate units. One or more unit doses containing the active ingredients may be comprised in a cartridge, pack or dispenser device. Such a cartridge, pack or dispenser device can be accompanied by instructions for administration of the composition. A dosage regimen may involve the administration of one or more unit doses per serving, typically 1-5 unit doses per serving.

Given its low or reduced volume, the composition is preferably in the form of a solid or semi-solid dosage unit form. The unit dose is preferably a tablet, gel, including soft gel, dragee, pill, capsule, granule, pellet, or (powder) sachet, squeeze packet, suitable for oral administration, wherein the active ingredients are present in a therapeutically effective amount, and combined with one or more diluents, gelling agents or excipients which are inactive ingredients to dilute or give the active ingredients form or consistency, and are effective to deliver the active ingredients to a human as prescribed by a physician.

Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl cellulose, sodium carboxymethyl cellulose, and/or polyvinylpyrrolidone (PVP). Other suitable pharmaceutical carriers and their formulations are described in Remington: The Science and Practice of Pharmacy 1995, edited by E. W. Martin, Mack Publishing Company, 19th edition, Easton, Pa. If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum Arabic, talc, polyvinyl pyrrolidone, carbopol gel, polyethylene glycol, and/or titanium dioxide, Fe oxides, lacquer solutions, and suitable organic solvents or solvent mixtures. Dyestuffs or pigments may be added to the tablets or dragee coatings for identification or to characterize different combinations of active compound doses. Gelatine or plasticizers such as glycerol or sorbitol are often applied to obtain capsules. Capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, emulsifiers, e.g. soy lecithin, liquid paraffin, or liquid polyethylene glycols. In addition, stabilizers may be added.

The daily dosage will be adjusted to the individual requirements in each particular case. It may involve the administration of 1-20 unit doses, preferably 2-10 unit doses per day. One of ordinary skill in treating diseases described herein will be able, without undue experimentation and in reliance on personal knowledge, experience and the disclosures of this application, to ascertain a therapeutically effective amount of the compounds of the present invention for a given disease and patient. Based thereon, the skilled person can determine the amount of unit doses to be administered per serving and per day. However, further on in the text, daily dosages are defined which may be of help in determining the number of unit doses to be administered.

The reduced or low volume composition according to the present invention may be characterized by one or more of the following features which all relate to the reduced size of the composition:

In an embodiment (a), the composition preferably has a weight of 200-3000 mg per unit dose, more preferably 300-2000 mg per unit dose, most preferably less than 1000 mg per unit dose.

In an embodiment (b), the caloric volume of the composition of the invention is preferably lower than 50 kcal per unit dose, more preferably lower than 40 kcal per unit dose, most preferably less than 30 kcal per unit dose. Additionally or alternatively, it is especially preferred that the energy content of the composition is less than 10 kcal/g, more preferably less than 5 kcal/g, most preferably less than 3 kcal/g. These numbers apply to the solid weight of the composition, prior to any optional reconstitution in liquid.

In an embodiment (c), the low or reduced volume composition of the invention preferably has a volume between 0.1 and 10 ml ($cm^3$) per unit dose, more preferably 0.2-8 ml, most preferably at least 0.5 ml, in particular 1-5 ml.

In a preferred embodiment, the low volume composition is characterized by two, more preferably all three of the aforementioned features of (a) weight, (b) energy content and (c) volume.

DHA, EPA

The present invention comprises the use of docosahexaenoic acid (22:6 ω-3; DHA) and/or eicosapentaenoic acid (20:5 ω-3; EPA). Preferably the present composition contains at least DHA, more preferably DHA and EPA.

In a further aspect the present composition preferably contains a significant amount of EPA. EPA is converted to DPA (ω-3), increasing subsequent conversion of docosapentaenoic acid (22:5 ω-3; DPA) to DHA in the brain. Hence, the present composition preferably contains a significant amount of EPA, so to further stimulate in vivo DHA formation.

The DHA and/or EPA are preferably provided as triglycerides, diglycerides, monoglycerides, free fatty acids or their salts or esters, phospholipids, lysophospholipids, glycerol ethers, lipoproteins, ceramides, glycolipids or combinations thereof. Preferably, the present composition comprises at least DHA in triglyceride form.

In terms of daily dosage, the present method preferably comprises the administration of 50-5000 mg (DHA+EPA) per day, more preferably 100-3000 mg per day, most preferably 200-1000 mg per day. DHA is preferably administered in an amount of 50-4000 mg per day, more preferably 100-2500 mg per day, most preferably 200-1000 mg per day. If at all, EPA is preferably administered in an amount of 50-4000 mg per day, more preferably 100-2500 mg per day, most preferably 200-1000 mg per day. These amounts of EPA apply if it is used alone or in combination with DHA.

In terms of unit dosage, the proportion of (DHA+EPA) of the total fatty acids is preferably 5-95 wt. %, more preferably 10-80 wt. %, most preferably 15-70 wt. %. The present composition preferably comprises 5-95 wt. % DHA based on total fatty acids, preferably 10-75 wt. % DHA based on total fatty acids, more preferably 10-60 wt. % DHA based on total fatty acids. The present composition preferably comprises 5-95 wt. % EPA based on total fatty acids, preferably 10-75 wt. % EPA, most preferably 15-60 wt %, based on total fatty acids.

The ratio of the weights of DHA to EPA is preferably larger than 1.0, more preferably 1.2-10, more preferably 2-8. The above-mentioned ratios and amounts take into account and optimise several aspects, including taste (too high LCP levels reduce taste, resulting in a reduced compliance), balance between DHA and precursors thereof to ensure optimal effectiveness in relation to maximum dosage and in view of the low-volume product formulations of the invention.

The present method preferably comprises the administration of DHA, preferably in a composition comprising 50-1000 mg DHA per unit dose, more preferably 100-500 mg DHA per unit dose, most preferably 100-400 mg DHA per unit dose, at least 200 mg DHA per unit dose. A unit dose according to the present method preferably comprises 5-95 wt % DHA, more preferably 10-75 wt % DHA, more preferably 20-60 wt %, most preferably 25-50 wt %, based on the total dry weight of the unit dose. The preferred ranges per unit dose mentioned in this paragraph for DHA also apply to EPA, if present.

The present composition preferably contains a very low amount of arachidonic acid (AA; 22:4 ω-6). The arachidonic acid is believed to counteract the effects of the present composition. The present subject normally ingests sufficient (precursors of) AA, and an excess daily dosage may stimulate inflammatory responses, inhibiting daily activities. Preferably the weight ratio DHA/AA in the present composition is at least 5, preferably at least 10, more preferably at least 15. The present method preferably comprises the administration of a composition comprising less than 5 wt. % arachidonic acid based on total fatty acids, more preferably below 2.5 wt. %. The ratio omega-6/omega-3 fatty acids, in the present product, are preferably below 0.5, more preferably below 0.2.

The present composition preferably contains at least one oil selected from fish oil, algal oil, genetically modified plants containing DHA, and egg lipids. Preferably the present composition contains fish oil comprising DHA and EPA.

Nucleotides

The present composition preferably comprises uridine and/or an equivalent thereof, preferably at least one uridine or an equivalent thereof selected from the group consisting of uridine (i.e. ribosyl uracil), deoxyuridine (deoxyribosyl uracil), uridine phosphates (UMP, dUMP, UDP, UTP), nucleobase uracil and acylated uridine derivatives. Preferably the present composition comprises an uridine phosphate selected from the group consisting of uridine monophosphate (UMP), uridine diphosphate (UDP) and uridine triphosphate (UTP). Most preferably the present composition comprises UMP, as UMP is most efficiently being taken up by the body. Preferably at least 50 wt. % of the uridine in the present composition is provided by UMP, more preferably at least 75 wt. %, most preferably at least 95 wt. %.

The present method preferably comprises the administration of uridine (the cumulative amount of uridine, deoxyuridine, uridine phosphates, nucleobase uracil and acylated uridine derivatives) in an amount of 0.01-6 g per day, preferably 0.1-2 g per day, more preferably 0.2-1 g per day.

Preferably the present composition comprises uridine phosphate, preferably uridine monophosphate (UMP). The UMP is very efficiently taken up by the body. Hence, inclusion of UMP in the present composition enables a high effectivity at the lowest dosage and/or the administration of a low volume to the subject.

The present method preferably comprises the administration of a composition comprising uridine in an amount of 10-1000 mg per unit dose, preferably 20-600 mg per unit dose, more preferably 50-400 mg per unit dose, in particular at least 100 mg per unit dose, based on the dry weight of the unit dose. The relative amount of uridine and its equivalents is preferably 1-50 wt %, more preferably 2-40 wt %, most preferably 5-25 wt %, based on the total dry weight of the unit dose.

The required unit and daily dosages of the equivalents on a weight base can be calculated from the dose for uridine by taking equimolar amounts using the molecular weight of the equivalent and of uridine.

The present method preferably comprises the administration of uridine monophosphate (UMP) in an amount of 0.01-3 g per day, preferably 0.1-2 g per day, more preferably 0.2-1 g per day. Preferably 1-37.5 mg UMP per kilogram body weight is administered per day. The required unit and daily dosages of the equivalents on a weight base can be calculated from the dose for UMP by taking equimolar amounts using the molecular weight of the equivalent and of UMP, the latter being 324 Dalton.

In a further preferred embodiment the present composition preferably does not contain high amounts of other nucleotides. Hence, preferably the weight ratio adenosine/uridine in the present composition is below 0.1, more preferably below 0.01, most preferably 0. Preferably the weight ratio guanosine/uridine in the present composition is below 0.1, more preferably below 0.01, most preferably 0. Preferably the weight ratio inosine/uridine in the present composition is below 0.1, more preferably below 0.01, most preferably 0.

In the composition, it is preferred that the weight ratio of DHA and/or EPA to uridine and its equivalents, recalculated in equimolar amounts of UMP, is at least 1, more preferably at least 1.5. More preferably, DHA is predominant in the composition over uridine and its equivalents in terms of weight.

The composition may further include cytidine. Preferably the weight ratio of uridine to cytidine is larger that 1.0, more preferably 2.0, most preferably more than 5.0. The term uridine as used herein relates to uridine and/or equivalents thereof. The term cytidine as used herein relates to cytidine and/or equivalent thereof. Although cytidine is a precursor of uridine, which passes the blood brain barrier, it is more efficient and effective to include uridine in the present composition.

Tocopherol

The present composition further contains a tocopherol and/or an equivalent thereof, including methylated phenols derived there from. Tocopherols contain a chromanol ring, with a hydroxyl group that can donate a hydrogen atom to reduce free radicals and a hydrophobic side chain. The definition also includes tocotrienols, which have structures corresponding to tocopherol, except with an unsaturated bond in each of the three isoprene units that form the hydrocarbon tail. Tocopherols have a saturated phytyl tail.

The term "a tocopherol and/or an equivalent thereof", as used in this description, comprises tocopherols, tocotrienols, pharmaceutical and/or nutritional acceptable derivatives thereof and any combination thereof. Tocopherols and tocotrienols occur in alpha, beta, gamma and delta forms, determined by the number of methyl groups on the chromanol ring.

Each form has slightly different biological activity. An example of a pharmaceutical and/or nutritional acceptable derivative is a salt such as, for instance an acetate or succinate.

More preferably, the composition comprises tocopherol family members, more preferably alpha-tocopherol and its nutritional and/or pharmaceutically acceptable equivalents.

The amount of tocopherol is preferably 0.1-50 mg per unit dose, more preferably 1-40 mg per unit dose, most preferably less than 30 mg per unit dose. These numbers correspond to the amount of alpha-tocopherol. The required unit and daily dosages of the equivalents of alpha-tocopherol on a weight base can be calculated using, for instance, the table provided below. Therein, the amount of 1.0 mg of the tocopherol equivalent is recalculated in terms of "x" mg α-TE. R stands for the side groups attached to the phenyl, which can be methyl or hydrogen, depending on the tocopherol at dispute.

| Tocopherol form | x mg α-TE | IU vitamin E |
|---|---|---|
| RRR-α-tocopherol (d-α-tocopherol) | 1.0 | 1.49 |
| all rac-α-tocopherol (d,1-α-tocopherol) | 0.74 | 1.10 |
| RRR-α-tocopheryl acetate | 0.91 | 1.36 |
| all rac-α-tocopheryl acetate | 0.67 | 1.00 |
| RRR-α-tocopheryl succinate | 0.81 | 1.21 |
| all rac-α-tocopheryl succinate | 0.60 | 0.89 |
| RRR-β-tocopherol | 0.50 | 0.75 |
| RRR-γ-tocopherol | 0.10 | 0.15 |
| RRR-δ-tocopherol | 0.03 | 0.05 |
| RRR-α-tocotrienol | 0.50 | 0.75 |
| RRR-β-tocotrienol | 0.05 | 0.08 |

Proteinaceous Content

The present composition preferably has a low proteinaceous content, including free amino acids, peptides, (un)hydrolysed proteins, and salts thereof. It is preferred that a unit dose contains less than 300 mg, more preferably less than 200 mg, most preferably less than 100 mg of proteinaceous material. Most preferably, the composition is at least free from peptides and proteins, and hydrolysates thereof.

In one embodiment, the proteinaceous content of the composition of the invention is less than 20 wt %, more preferably less than 10 wt %, based on the dry weight of the composition.

Additionally or alternatively, the weight ratio of proteinaceous material over the sum of DHA, EPA and uridine and its equivalents is preferably less than 1, more preferably less than 0.5, most preferably less than 0.25, particularly less than 0.1.

Other Therapeutics

It may be appropriate to include any therapeutic which can be used to protect an individual against any of the conditions or diseases discussed herein, and may include a drug. Such therapeutic compounds will be well known to the skilled person for the particular disease or condition treated.

The active ingredients of the invention may be provided as salts with pharmaceutically compatible counter ions. Pharmaceutically compatible salts may be formed with many acids, including but not limited to hydrochloric, sulphuric, acetic, lactic, tartaric, malic, succinic, etc. Salts tend to be more soluble in aqueous or other protonic solvents that are the corresponding free base forms.

Uses

The invention pertains to the use of the above-defined composition for preventing and/or treating memory decline and/or cognitive dysfunction, Alzheimer's and/or dementia. In the context of the invention, "dementia" is especially understood "senile dementia". Senile dementia or dementia is considered to comprise Alzheimer's disease (AD).

The invention also pertains to the use of said composition for reducing neurodegeneration and/or reducing the deposition of (abeta) plaques in the brain, and/or for promoting or supporting healthy brain function.

In one embodiment the present composition is administered to a prodromal dementia patient and/or prodromal Alzheimer patient. A "prodromal dementia patient" is a person who does not suffer from a senile dementia as defined above, but has an increased likelihood to develop senile dementia. Likewise a "prodromal Alzheimer patient" is a person who does not suffer from AD, but has an increased likelihood to develop AD. The diagnostic tools that are used to classify the patients as prodromal patients are described below and include an accurate diagnosis of brain lesions and biochemical problems and careful setting of criteria.

Prodromal patients are defined to be persons that score positively on at least one, preferably at least two, more preferably at least three of the following criteria:

- a level of more than 350 ng Total-tau per litre cerebrospinal fluid (CSF);
- a weight ratio of abeta-42/Phospho-tau-181 of less than 6.5 in CSF;
- presence of medial temporal lobe (MTL) atrophy, existing of volume loss of hippocampus, entorhinal cortex, or amygdala evidenced on Magnetic Resonance Imaging (MRI) with either qualitative ratings using visual scoring (referenced to well characterised population with age norms) or quantitative volumetry of regions of interest (referenced to well characterized population with age norms)
- presence of fronto-temporal lobe (FTL) atrophy evidenced on MRI with qualitative ratings or quantitative volumetry;
- a level of more than 25 pg F2-iso-prostane (F2-IsoP, isoprostane 8,12-iso-iPF2alpha-VI) per mL CSF.

Further explanations of the significance of concentrations of T-tau, P-tau181, Abeta42 and F2-Isoprostane in CSF for future development of Alzheimer's disease can be found in: Hansson O, Zetterberg H, Buchhave P, Londos E, Blennow K, Minthon L (2006) Association between CSF biomarkers and incipient Alzheimer's disease in patients with mild cognitive impairment: a follow-up study. Lancet Neurol 5:228-234; and in Pratico D, Clark C M, Liun F, Lee V Y M, Trojanowski J Q (2002) Increase in brain oxidative stress in mild cognitive impairment: a possible predictor of Alzheimer disease. Arch Neurol 59:972-976.

It should be noted that the score of these prodromal patients in tests relating to the presence of episodic memory impairment or other tests suitable for the judgment of the presence of the neurological disease, does not meet the criteria for diagnosing a neuro-logical disease like Alzheimer's disease.

The invention also pertains to the treatment of age-associated memory impairment (AAMI), Mild Cognitive Impairment (MCI), significant episodic memory impairments and to treating elderly with memory and/or cognitive impairments, using the aforementioned composition.

It is also an objective of the invention to provide a method for supporting brain health and/or reducing plaque burden and/or reducing neurodegeneration in a subject in need thereof, such as a subject suffering from one of the aforementioned disorders, by administering to said subject the low or reduced volume composition as defined above.

Trademarks which provide an implicit link between the composition and one or more of the intended uses as defined above are also considered to fall within the scope of the invention.

EXAMPLES

Capsule Composition

A capsule was prepared comprising a blend of 500 mg marine oils, comprising 60 mg docosahexaenoic acid. The amount of EPA was 90 mg. It included 150 mg uridine monophosphate and 6 mg alpha-tocopherol. All numbers were based on the dry weight of the capsule. The total weight of the capsule was 1.1 g. The capsule further contained glycerine, polysorbate 40, and calcium alginate.

One to four of these capsules were recommended daily for preferably more than one month.

Experiment 1

The current experiment tested whether UMP, DHA, UMP+DHA and UMP+DHA+alpha-tocopherol could reduce abeta plaques and neurodegeneration in Alzheimer's disease (AD) model mice, the APP/PS1 mice. These mice start showing plaques in their brains as early as 4-5 months of age and are considered a good model for AD in scientific literature.

The mice were fed diets enriched in (1) UMP, (2) DHA, (3) UMP+DHA or (4) UMP+DHA+alpha-tocopherol starting at 3 months of age, just before the first plaques become apparent. The diets were fed for a period of 3 months until the age of 6 months. Thereafter the mice were sacrificed and their brains processed for abeta plaque analyses and neurodegeneration analyses. The brain was cut into thin slices using a vibratome and the slices were stained for abeta using an antibody recognizing human abeta and for neurodegeneration using the amino-cupric staining The total number of plaques in the hippocampus was counted and the total surface of the area covered by plaques (plaque burden) was determined. Total surface area covered with neuritic plaques (staining positive for amino-cupric) was determined to measure the level of neurodegeneration.

Results

The results are shown in FIGS. 1 and 2, for plaque burden and neurodegeneration, respectively. In each case, Figure "A" shows the effect of the composition (4) in accordance with the invention, and Figure "B" shows the effect of individual nutrients. "Multi" refers to composition (4), containing DHA, UMP and alpha-tocopherol.

Figure 1B:
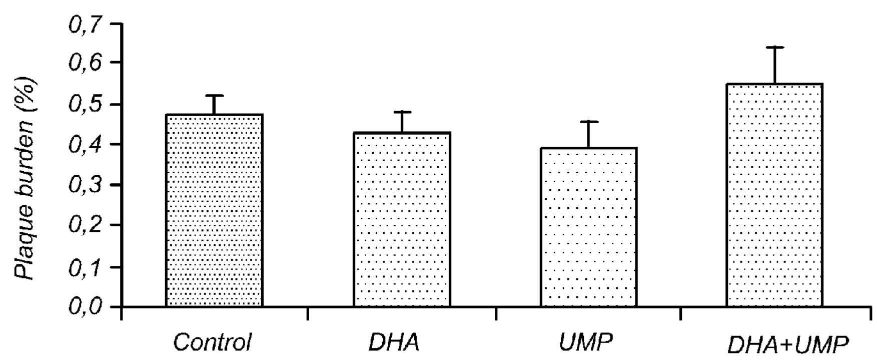
FIG. 1B shows the percent plaque burden in the hippocampus of mice fed a diet comprising UMP, DA, or UMP+DHA compared to a control diet.

FIG. 1A shows that intervention reduced plaque burden in the hippocampus of APP/PS1 mice. When UMP or DHA were fed, plaque burden was not affected. The combination of UMP and DHA resulted in an increase in plaque burden (FIG. 1B).

Figure 2A:
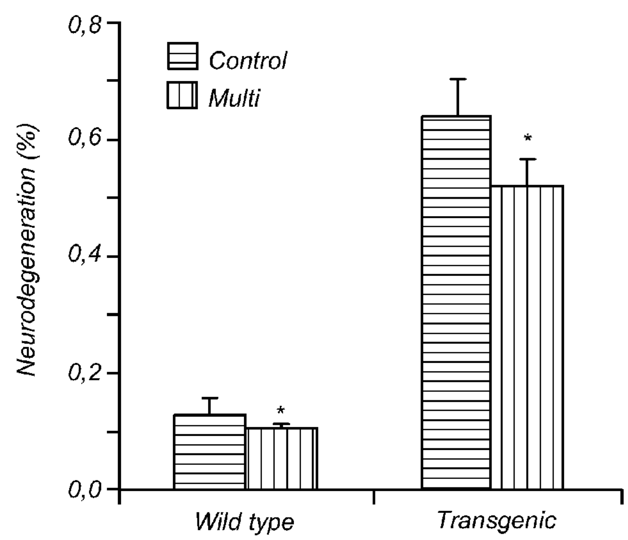
FIG. 2A shows the percent neurodegeneration in wild-type and APP/PS1 transgenic mice fed a control diet or one comprising UMP, DHA, and alpha-tocipherol ("multi").
Figure 2B:
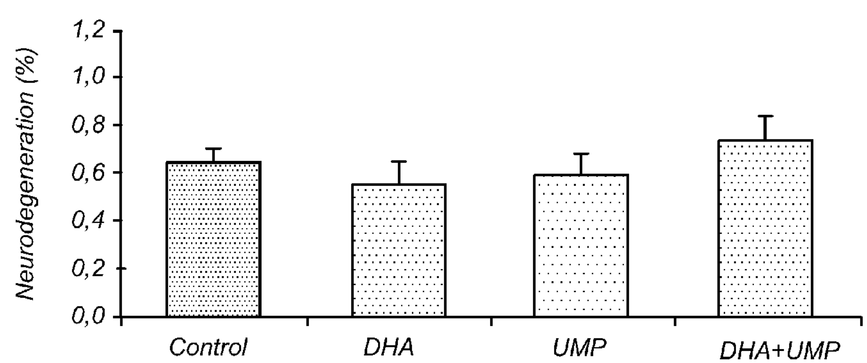
FIG. 2B shows the percent neurodegeneration in mice fed a diet comprising UMP, DA, or UMP+DHA compared to a control diet.

Mice fed diet (4) showed lower levels of neurodegeneration compared to control diet fed mice (FIG. 2A). Mice fed UMP or DHA did not differ from the control whereas UMP+DHA mice tended to display higher levels of neurodegeneration (FIG. 2B).

From this study it was concluded that intervention with the composition of the invention is effective in reducing abeta production, reducing abeta plaque formation and reducing neurodegeneration. Individual nutrients either have no effect on these parameters or they induce further deterioration compared to mice fed a control diet.

Experiment 2

Alzheimer's disease is characterized by a loss of cognitive abilities which can be explained by a loss of communication between neuronal cells leading to a reduction in neuronal functioning and eventually neuronal cell death (neurodegeneration). Neuronal communication is dependent upon the connections (synapses) between neurons where neurotransmitters from the pre-synaptic neuron are released and bind to receptors on the post-synaptic neuron. Receptor function is an important factor in neuronal communication. By improving receptor function, neuronal cells would communicate more effectively which would be reflected by e.g. lower levels of a receptor agonist to induce the same level of stimulation.

In the experiment described below, neuronal pheochromocytoma cells (PC12 cells) were used to study the effect of incubation with nutrients (docosahexaenoic acid (DHA), uridine monophosphate (UMP), alpha-tocopherol (vitamin E) or combinations thereof) on receptor functionality.

To this end, the cells were cultured in a 96-wells format and incubated with control medium, control medium+alpha-tocopherol, control medium+UMP, control medium+DHA+alpha-tocopherol, or control medium+DHA+UMP+alpha-tocopherol. Incubation with DHA alone led to cell death. After 1 day of incubation the medium+additions were replaced by control medium and the cells were stimulated with 50 μM oxotremorine, an agonist at the muscarinic acetylcholine receptor, involved in learning and memory. Oxotremorine induces a depolarization of the membrane which can be measured as a change in membrane potential. At a fixed dose of the agonist, increases in membrane potential are thought to reflect improvements in receptor functioning.

Results

Figure 3:
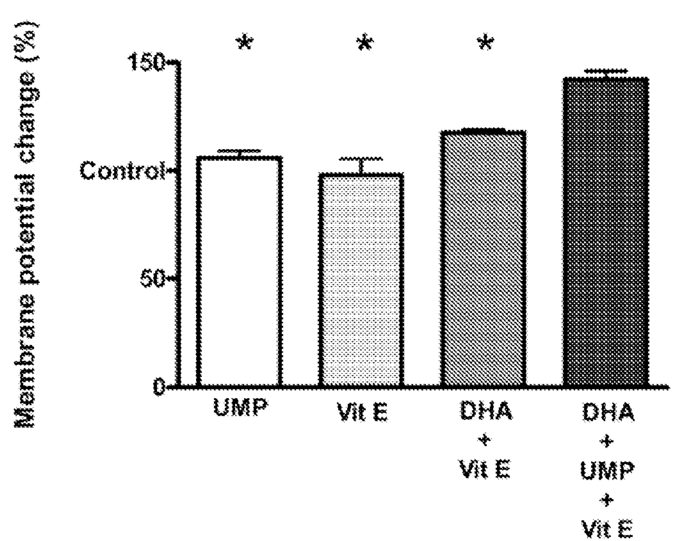
FIG. 3 shows the change in membrane potential of cells incubated with UMP (first bar); alpha-tocopherol (second bar); DHA+alpha-tocopherol (third bar); and DHA+UMP+ alpha-tocopherol.

FIG. 3 shows the results in terms of membrane potential change under the different incubation conditions. The "*" marks that the result was significantly different from DHA+UMP+alpha-tocopherol (Vit E).

All data are plotted as percentage change in membrane potential compared to control conditions. The results show that cells incubated with UMP (first bar), alpha-tocopherol (second bar), and DHA+alpha-tocopherol (third bar) did not affect membrane potential change. On the other hand, cells incubated with the combination according to the invention of DHA+UMP+alpha-tocopherol did show an increase in membrane potential change ($F=19.9$; $p=0.000$).

The present results indicate that incubation with a combination of alpha-tocopherol, DHA and UMP synergistically improved receptor functioning. Vitamin E and UMP alone, and the combination of DHA+alpha-tocopherol had no effect on receptor ceptor function. These results suggest that neuronal cells in the brain of Alzheimer's disease patients may benefit from the combined supplementation of DHA, UMP and alpha-tocopherol by improving receptor function and neuronal communication to support cognitive abilities and to reduce neurodegeneration.

The invention claimed is:

1. A composition comprising (i) uridine in nucleobase, nucleoside and/or nucleotide form;

(ii) docosahexaenoic acid (DHA) and/or eicosapentaenoic acid (EPA); and (iii) a tocopherol and/or an equivalent thereof, wherein said composition has:

a) a weight of 200-3000 mg per unit dose;

b) an energy content of less than 50 kcal per unit dose; and/or c) a volume between 0.1 and 10 ml per unit dose.

2. The composition according to claim 1, wherein the tocopherol and/or an equivalent thereof is alpha-tocopherol.

3. The composition according to claim 1, wherein the unit dose is a tablet, gel, dragee, pill, capsule, granule, pellet, or sachet.

4. The composition according to claim 1, comprising 5-75 wt % DHA, based on the dry weight of unit dose.

5. The composition according to claim 1, comprising 50-1000 mg DHA per dry weight of unit dose.

6. The composition according to claim 1, comprising uridine in an amount of 10-1000 mg uridine in nucleobase, nucleoside and/or nucleotide form per dry weight of unit dose.

7. The composition according to claim 1, comprising uridine and its equivalents in an amount of 1-50 wt %, based on the dry weight of unit dose.

8. The composition according to claim 1, wherein the weight ratio of (ii) to (i) is at least 1.

9. The composition according to claim 1, comprising less than 300 mg proteinaceous material per unit dose.

10. The composition according to claim 1, comprising less than 20 wt % of proteinaceous material based on the dry weight of the composition.

11. The composition according to claim 1, wherein the weight ratio of proteinaceous material over the sum of (i) and (ii) is less than 1.

12. A method of treatment and/or prevention of a disorder selected from the group of memory dysfunction, cognitive dysfunction, Alzheimer's and dementia, comprising administering to a patient in need thereof a composition according to claim 1.

13. The method according to claim 12, wherein administration of the composition reduces neurodegeneration.

14. The method according to claim 12, wherein administration of the composition reduces the deposition of plaques in the brain.

15. A cartridge, pack or dispenser device comprising one or more of the compositions according to claim 1, accompanied by instructions for administration of said composition.

16. A method for reducing neurodegeneration and/or the deposition of plaques in the brain and/or for promoting, optimizing and/or supporting brain function or brain health in a subject in need thereof, the method comprising administering to said subject a composition according to claim 1.

* * * * *